United States Patent [19]

Salimbeni et al.

[11] Patent Number: 6,096,754
[45] Date of Patent: Aug. 1, 2000

[54] N-3 SUBSTITUTED PYRIMIDIN-4-ONES WITH AII ANTAGONISTIC ACTIVITY

[75] Inventors: Aldo Salimbeni; Davide Poma; Renato Canevotti, all of Milan, Italy

[73] Assignee: Istituto Luso Farmaco D'Italia S.p.A., Milan, Italy

[21] Appl. No.: 09/171,265
[22] PCT Filed: Apr. 11, 1997
[86] PCT No.: PCT/EP97/01817
§ 371 Date: Oct. 16, 1998
§ 102(e) Date: Oct. 16, 1998
[87] PCT Pub. No.: WO97/40040
PCT Pub. Date: Oct. 30, 1997

[30] Foreign Application Priority Data

Apr. 19, 1996 [IT] Italy ................................. MI96A0756

[51] Int. Cl.⁷ ................................................. C07D 403/06
[52] U.S. Cl. ........................................... 514/269; 544/319
[58] Field of Search ...................................... 544/319, 310, 544/316, 321; 514/269, 319, 337

[56] References Cited

U.S. PATENT DOCUMENTS 5,565,464  10/1996  Salimbeni et al. ...................... 514/269

FOREIGN PATENT DOCUMENTS 0 465 323    1/1992   European Pat. Off. .
WO 94/03449  2/1994   Italy .
93/03018     2/1993   WIPO .

*Primary Examiner*—Mukund J. Shah
*Assistant Examiner*—Sudhaber B. Patel
*Attorney, Agent, or Firm*—Griffin, Butler, Whisenhunt & Szipl, LLP

[57] ABSTRACT

N-3-substituted pyrimindin-4-ones with angiotension II (AII) antagonistic activity are characterized by the presence of a heterocyclic moiety bound to the 3-position of the pyrimidinone ring and a biphenylmethyl moiety bound to the 5-position of the pyrimidinone ring. Preferred heterocyclic moieties include furan, thiophene, thiazole, isothiazole, oxazole, isoxazole, pyridine, pyrimidine, pyrazine, and pyridazine rings.

7 Claims, No Drawings

N-3 SUBSTITUTED PYRIMIDIN-4-ONES WITH AII ANTAGONISTIC ACTIVITY

The present invention relates to N-3 substituted pyrimidin-4-ones with AII antagonistic activity.

The modulation of the renin-angiotensin system (RAS) by means of antagonism of angiotensin II (AII) at the receptor level, recently proved to be a valuable alternative to renin inhibitors or to ACE inhibitors, in the control of blood pressure. Examples of compounds having antagonistic activity of angiotensin II are disclosed in EP-A-0465323. Said compounds are derivatives of 5-diphenylmethyl-pyrimidine. A preceding patent application PCT WO 93/03018 in the Applicant's name disclosed pyrimidinone derivatives having antagonistic properties on the AII receptor, which derivatives have, in particular on the nitrogen atom at the 3-position of the pyrimidinone ring, a benzyl, thienylmethylene or furanylmethylene, substituted by a carboxylic or ester group.

The present invention relates to novel derivatives with a pyrimidinone structure having AII-antagonistic properties, characterized in particular, compared with the above described structures, by the presence of a different heterocycle bound to the 3-position of the pyrimidinone ring and/or of a different substituent bound to the heterocycle itself.

The compounds of the invention have the general formula I

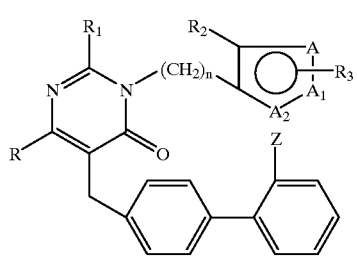

(I)

wherein:

R can be a straight, branched or cyclic lower alkyl of 1 to 5 carbon atoms, optionally substituted by a $OR_4$ group, wherein $R_4$ can be hydrogen or a $C_1$–$C_4$ alkyl; or a lower alkenyl group of 1 to 5 carbon atoms, $R_1$ and $R_3$ can be independently hydrogen or a $C_1$–$C_4$ alkyl, $R_2$ can be a CN group; a $CH_2OR_5$ group wherein $R_5$ can be hydrogen or a $C_1$–$C_4$ alkyl; a $COR_6$ group wherein $R_6$ can be a $C_1$–$C_4$ alkyl or a $NR_7R_8$ group wherein $R_7$ and $R_8$, which are the same or different, can be hydrogen, $C_1$–$C_4$ alkyl, phenyl or benzyl, n can be 1 or 2, A, $A_1$, $A_2$, can be independently N,O,S atoms, or $(CH)_m$, wherein m=1,2, with the proviso that at least one be a heteroatom, and they form, together with two carbon atoms, a 5- or 6-membered heterocyclic ring.

Z can be a $COOR_9$ group, wherein $R_9$ can be hydrogen or a $C_1$–$C_4$ alkyl; a $NHSO_2CF_3$ group; a CN group; a $NO_2$ group; a $SO_2NHR_{10}$ group, wherein $R_{10}$ can be hydrogen, $COR_{11}$, wherein $R_{11}$ can be an optionally substituted phenyl, a $C_1$–$C_4$ alkyl, a $C_1$–$C_4$ alkoxy, or $CONHR_{12}$, wherein $R_{12}$ is a straight or branched $C_1$–$C_4$ alkyl; a tetrazol-5-yl group optionally protected by a group preferably selected from the following: triphenylmethyl, tert-butyl, $C_1$–$C_4$ alkoxymethyl, 4-methoxybenzyl, 2,4,6-trimethylbenzyl, tetrahydropyranyl or 2-trimethylsilylethyl.

In the compounds I, R is preferably a straight, branched or cyclic lower alkyl of 1 to 5 carbon atoms, optionally substituted by a OR4 group, wherein $R_4$ can be hydrogen or a $C_1$–$C_4$ alkyl, and, more preferably, R is a lower alkyl of 1 to 5 carbon atoms;

$R_2$ is preferably a CN group, or a $COR_6$ group wherein $R_6$ can be a $C_1$–$C_4$ alkyl or a $NR_7R_8$ group wherein $R_7$ and $R_8$, which are the same or different, can be hydrogen, $C_1$–$C_4$ alkyl, and more preferably, is selected from a CN group or a group $CONR_7R_8$ wherein $R_7$ and $R_8$, which are the same or different, can be hydrogen or $C_1$–$C_4$ alkyl, n is preferably the integer 1;

A, $A_1$ and $A_2$ are preferably selected so as to form, with the carbon atoms which they are bound to, the following heterocyclic rings: furan, thiophene, thiazole, isothiazole, oxazole, isoxazole, pyridine, pyrimidine, pyrazine, pyridazine, Z is preferably a $COOR_9$ group, wherein $R_9$ can be hydrogen or a $C_1$–$C_4$ alkyl; a group $NHSO_2CF_3$; a tetrazol-5-yl group optionally protected by a group preferably selected from the following: triphenylmethyl, tert-butyl, $C_1$–$C_4$ alkoxymethyl, 4-methoxybenzyl, 2,4,6-trimethylbenzyl, tetrahydropyranyl or 2-trimethylsilylethyl and, more preferably, is a tetrazol-5-yl group.

The compounds of the invention form, with various inorganic and organic acids and bases, pharmaceutically acceptable salts which also are object of this invention.

Said salts include ammonium salts, salts with alkali metals such as sodium and potassium, with alkaline-earth metals such as calcium and magnesium, with organic bases, such as dicyclohexylamine, N-methyl-D-glucamine, with amino acids such as arginine, lysine and the like.

The novel compounds can be prepared according to various processes. A first method comprises the reaction of compounds of general formula II,

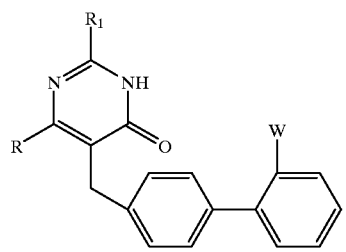

(II)

wherein:

R and $R_1$ have the same meanings as in formula I,

W can be a CN group, a $C_1$–$C_4$ alkoxycarbonyl, a nitro group, a suitably protected $SO_2NH_2$ group, a tetrazol-5-yl protected with a suitable group selected from the following: triphenylmethyl, tert-butyl, $C_1$–$C_4$ alkoxymethyl, 4-methoxybenzyl, 2,4,6-trimethylbenzyl, tetrahydropyranyl or 2-trimethylsilylethyl, and compounds of formula III

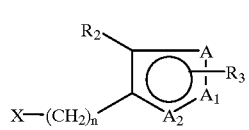

(III)

wherein:

$R_3$, A, $A_1$, $A_2$ and n have the same meanings as in formula I,

X can be a halogen such as chlorine, bromine, iodine or a mesylate or tosylate group, $R_2$ has the same meanings as in formula I, taking into account that a suitable protection will be necessary for some meanings which are incompatible with the reaction conditions, to give compounds of formula I wherein Z is the same as W, and subsequently transforming, if necessary, the W residue into the Z residue, wherein Z can be a carboxylic group, a $NHSO_2CF_3$ group, a tetrazol-5-yl group or a $SO_2NHR_{10}$ group wherein $R_{10}$ has the same meanings as in formula I.

The compounds of formula II can be prepared for example, by cyclization of a suitable amidine with the appropriate 1,3-dicarbonyl derivative, as described for example in the articles by A. Salimbeni et al. J. Med. Chem. 1995, 38, 4806–4820 or by E. Nicolaï et al. J. Med. Chem. 1994, 37, 2371–2386.

The compounds of formula III are prepared in their turn from simple precursors, according to procedures known in literature, as described for example by M. Janda et al. in Coll. Czech. Chem. Comm., 1974, 39, 959.

The compounds of formula I, wherein Z is alkoxycarbonyl, can be transformed into the corresponding carboxylic acids, by acid or alkali hydrolysis.

The compounds of formula I, wherein Z is a CN group or a substituted 5-tetrazolyl group, can be converted into the corresponding compounds wherein Z is a 5-tetrazolyl group with one of the methods described in literature, such as those reported in "Protective group in organic synthesis", T. W. Green, P. G. M. Wuts, J. Wiley & Sons, 1991 or by A. Salimbeni et al. in J. Med. Chem., 1995, 38, 4806–20. From the compounds of formula I, wherein Z is a nitro group or a suitably protected $SO_2NH_2$ group, compounds of formula I wherein Z is respectively a $NHSO_2CF_3$ group or a $SO_2NHR_{10}$ group, can be prepared by methods known in literature.

Literature widely reports that the alkylation of bidentate systems, such as the compounds of formula II, usually results in mixtures of the N and O alkylation regioisomers. Thanks to the use of an organo-metallic compound such as butyllithium and of aprotic solvents such as THF or DME, preferably at the solvent boiling temperature, it has been possible to minimize the formation of the O alkylation regioisomer, with a resulting simplified working up and a marked increase in the yield.

A second method comprises a diaryl coupling reaction of the compounds of formula IV, prepared according to the procedures reported in Italian patent application MI 95 A 001485,

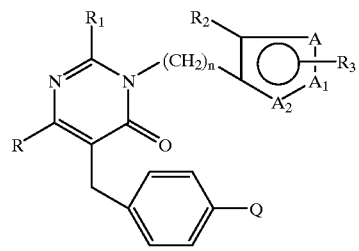

(IV)

wherein:

R, $R_1$, $R_2$, $R_3$, A, $A_1$, $A_2$ and n have the same meanings as in formula I, Q can be a halogen such as chlorine, bromine or iodine, a $OSO_2CF_3$ group or a $BR_{13}R_{14}$ group wherein $R_{13}$ and $R_{14}$ can be independently, hydroxy, alkoxy or they are bound together to form a cyclic structure of formula

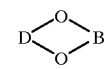

wherein D can be phenyl or $(CH_2)p$ with p=2–4, with compounds of formula V

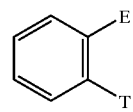

(V)

wherein:

E can be a CN group, a $C_1$–$C_4$-alkoxycarbonyl, a tetrazol-5-yl group protected with one of the groups as in formula I, a $SO_2NH$-tert-butyl group, T can be bromine, chlorine, iodine, $OSO_2CF_3$ or a $M(L)_q$ group wherein M is a metal such as Zn, Mg, Sn, Cu, L is a halogen such as chlorine or bromine or a $C_1$–$C_4$ alkyl and q can be 1 or 3, to give compounds of formula I wherein Z is the same as E, and subsequently transforming, if necessary, the E residue into the Z residue, wherein Z can be a carboxylic group, a tetrazol-5-yl group or a $SO_2NHR_{10}$ group wherein $R_{10}$ has the meanings as in formula I.

As reported in the first method for the preparation of the compounds of formula I, wherein Z is an alkoxycarbonyl group, CN, substituted tetrazol-5-yl or $SO_2NH$-tert-butyl, can be transformed into the compounds of formula I wherein Z is a carboxylic, tetrazol-5-yl or $SO_2NHR_{10}$ group.

The coupling reaction is carried out analogously to what widely reported in literature.

Alternatively, the compounds of formula I can be obtained from compounds of formula VI,

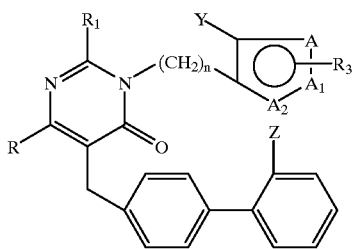

wherein:

R, $R_1$, $R_3$, A, $A_1$, $A_2$, Z and n have the meanings as in formula I,

Y can be a halogen such as bromine, chlorine, iodine; a carboxylic or a $C_1$–$C_4$ alkoxymethyl group, prepared for example as described in PCT WO 93/03018, or in the article by A. Salimbeni et al. in J. Med. Chem., 1995, 38, 4806–20. The procedures used for the transformation of compounds of formula VI into compounds of formula I are known in literature and, in so far as the other present functional groups allow, they are schematized in the following scheme:

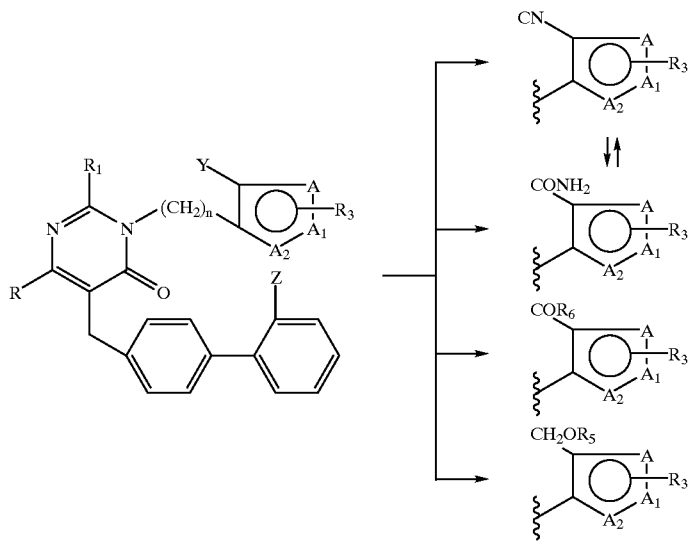

The novel compounds, compared with those described in PCT WO 93/03018, differ in the physico-chemical properties, such as lipophicity and water solubility and generally in that they are easier to prepare. For example, compound 2-[[4-butyl-2-methyl-6-oxo-5-[[2'-(1H-tetrazol-5-yl) [1,1'-biphenyl-4-methyl]-1(6H)-pyrimidinyl]methyl]-3-furancarbonitrile, described in example 2, shows a lipophilic degree about 6 times lower than that of the corresponding methyl 3-furancarboxylate (partition coefficient octanol/$H_2O$ 13.1 vs 79.3). Moreover, the alkali metal (sodium, potassium) salts thereof, unexpectedly proves to be extremely soluble in water. Finally, the application of the regioselective alkylation conditions, described in the first preparation method, causes a particularly significant increase in the yield.

For the characterization and the evaluation of the effectiveness of the compounds of the present invention, in vitro tests have been selected, such as the $^3$H-AII displacement from membranes of rat adrenal cortex, and in vivo, such as the inhibition of the A II-induced pressory response in the ganglio-blocked normotensive anaesthetized rat, according to what described by A. Salimbeni et al. in J. Med. Chem. 1995, 38, 4806–20. A number of compounds of the invention proved to be active in said tests, showing, for example, a Ki<1 nM in the receptor binding test and a $ED_{50}$<0,5 mg/kg in the in vivo test after i.v. administration.

The compounds (I) or the pharmaceutically acceptable salts thereof can be used in pharmaceutical preparations, alone or in a mixture with pharmaceutically acceptable excipients, for the oral or parenteral administrations. The pharmaceutical preparations can be in the solid form such as tablets, capsules or suppositories or in the liquid form, such as solutions, suspensions or emulsions.

Moreover, if administered parenterally, the pharmaceutical preparations can be in form of sterile solutions.

The compounds of general formula I can be administered in unit doses ranging from 1 to 100 mg daily to patients suffering from cardiac and vascular disorders, such as hypertension, acute and chronic cardiac decompensation, intraocular hypertension. However, a use can be envisaged also for other disorders, such as secondary hyperaldosteronism, pulmonary hypertension, renal diseases (glomerulonephritis, diabetic nephropathy) or vascular disorders (hemicrania, Raynaud's disease).

The following examples further illustrate the invention. M.p. are not corrected; the identity and purity of the substances were established by means of elementary analysis, $^1$H-NMR, IR and mass spectroscopies. Flash chromatographies were carried out on silica gel according to the procedures by W. C. Still, J. Org. Chem. 43, 2923 (1978).

EXAMPLE 1

2-[[4-butyl-2-methyl-6-oxo-5-[[2'-[1-(triphenylmethyl)-1H-tetrazol-5-yl]-[1,1'-biphenyl]-4-yl]methyl]-1(6H)-pyrimidinyl]methyl]-3-furancarbonitrile A suspension of 41.8 g of 6-butyl-2-methyl-5-[[2'-[1-triphenylmethyl)-1H-tetrazol-5-yl][1,'-biphenyl]4-yl] methyl]-pyrimidin-4(1H)-one in 230 ml of anhydrous THF, cooled at −5° C., is added drop by drop with 48.6 ml of 1.6

M butyllithium in hexane. After warming the solution to room temperature, a solution of 15.6 g of 2-(bromomethyl)-3-furancarbonitrile in 30 ml of anhydrous THF is added. After refluxing for 12 h, the reaction mixture is cooled to room temperature and treated with 10 ml of water, then poured into ice, neutralized at pH 7 with aqueous HCl, and extracted with $CH_2Cl_2$. The organic phase is dried over $Na_2SO_4$ and evaporated under reduced pressure. The resulting residue is recrystallized from AcOEt to give g 40.5 of an ivory solid (83% yield; m.p. 152–154° C. dec).

Analogously are prepared:

2-[[4-butyl-2-methyl-6-oxo-5-[[2'-[1-(triphenylmethyl)-1H-tetrazol-5-yl[1,1'-biphenyl]-4-yl]methyl]-1(6H)-pyrimidinyl]methyl]-3-thiophenecarbonitrile (m.p. 145–150° C. dec ($CH_3OH$));

2-[[4-butyl-2-methyl-6-oxo-5-[[2'-[1-(triphenylmethyl)-1H-tetrazol-5-yl][1,1'-biphenyl]-4-yl]methyl]-1(6H)-pyrimidinyl]methyl]-3-pyridinecarbonitrile;

4-[[4-butyl-2-methyl-6-oxo-5-[[2'-[1-(triphenylmethyl)-1H-tetrazol-5-yl][1,1'-biphenyl]-4-yl]methyl]-1(6H)-pyrimidinyl]methyl]-5-thiazolcarbonitrile;

2-[[4-butyl-2-methyl-6-oxo-5-[[2'-[1-triphenylmethyl)-1H-tetrazol-5-yl][1,1'-biphenyl]-4-yl]methyl]-1(6H)-pyrimidinyl]methyl]-2-pirazinecarbonitrile;

2-[[4-butyl-2-methyl-6-oxo-5-[[2'-nitro[1,1'-biphenyl]-4-yl]methyl]-1(6H)-pyrimidinyl]methyl-3-furancarbonitrile.

EXAMPLE 2

2-[[4-butyl-2-methyl-6-oxo-5-[[2'-(1H-tetrazol-5-yl)-[1,1'biphenyl]-4-yl]-methyl]-1(6H)-pyrimidinyl]methyl]-3-furancarbonitrile A suspension of 40 g of 2-[[4-butyl-2-methyl-6-oxo-5-[[2'[1-(triphenylmethyl)-1H-tetrazol-5-yl][1,1'-biphenyl]-4-yl]methyl]-1(6H)-pyrimidinyl]methyl]-3-furancarbonitrile in 400 ml of $CH_3OH$ is refluxed to complete reaction. The residue obtained by evaporation of the solvent under reduced pressure, is taken up into 330 ml of 1% NaOH and extracted with $Et_2O$. The aqueous phase is cooled at 5° C., acidified to pH 3 with 20% HCl and the resulting solid is filtered, washed thoroughly with water and dried under vacuum over $P_2O_5$. 26.2 g of a whitish solid are obtained (90% yield).

$^1$H-NMR δ0.92 (t,3H) 1.28–1.72 (m,4H), 2.62 (s,3H), 2.64 (t,2H), 3.91 (s,2H), 5.33 (s,2H), 6.60 (d,1H), 7.17 (q,4H), 7.41–7.53 (m,4H), 8.06–8.18 (m,1H).

Analogously are prepared:

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-thiophenecarbonitrile (m.p. 157–160° C. dec. ($Et_2O$));

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-pyridinecarbonitrile;

4-[[4-butyl-2-methyl-6-oxo-5-[[2'-(1H-tetrazol-5-yl)[1,1'-biphenyl]-4-yl]methyl]-1(6H)-pyrimidinyl]-methyl]-5-thiazolecarbonitrile;

2-[[4-butyl-2-methyl-6-oxo-5-[[2'-(1H-tetrazol-5-yl)[1,1'-biphenyl]-4-yl]methyl]1(6H)-pyrimidinyl]-methyl]-3-pirazinecarbonitrile;

2-[[4-butyl-2-methyl-6-oxo-5-[[2'-(1H-tetrazol-5-yl)[1,1'-biphenyl]-4-yl]methyl]-1(6H)-pyrimidinyl]-methyl]- 3-furancarboxamide (m.p. 190–195° C. dec. ($Et_2O$));

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-thiophenecarboxamide (m.p. 200–205° C. dec. ($Et_2O$));

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-pyridinecarboxamide;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-N-methyl-3-thiophenecarboxamide (m.p. 205–208° C. dec. ($Et_2O$));

2-[[4-butyl-2-methyl-6-oxo-5-[[2'-(1H-tetrazol-5-yl)[1,1'-biphenyl]-4-yl]methyl]-1(6H)-pyrimidinyl]-methyl]-N-methyl-3-pyridinecarboxamide (m.p. 206–209° C. dec. ($Et_2O$));

4-[[4-butyl-2-methyl-6-oxo-5-[[2'-(1H-tetrazol-5-yl)[1,1'-biphenyl]-4-yl]methyl]-1(6H)-pyrimidinyl]-methyl]-N-methyl-5-thiazolecarboxamide;

2-[[4-butyl-2-methyl-6-oxo-5-[[2'(1H-tetrazol-5-yl)[1,1'-biphenyl]-4-yl]methyl]-1(6H)-pyrimidinyl]-methyl]-3-thiophenemethanol (m.p. 168–170° C. dec. (AcOEt)).

EXAMPLE 3

2-[[4-butyl-2-methyl-6-oxo-5-[[2'-(1H-tetrazol-5-yl)-[1,1'-biphenyl]-4-yl]methyl]-1(6H)-pyrimidinyl] methyl]-3-furancarbonitrile potassium salt A solution of 23.3 g 2-[[4-butyl-2-methyl-6-oxo-5-[[2' (1H-tetrazol-5-yl)[1,1'-biphenyl]-4-yl]methyl]-1(6H)-pyrimidinyl]methyl]-3-furancarbonitrile in 80 ml of isopropanol, kept at 5° C. under stirring, is added, dropping slowly, with 2.94 g of 88% KOH dissolved in 2 ml of $H_2O$. After adding the first 0.5 ml cooling is interrupted and 1 h from the end of the addition, which lasted 30 minutes, the precipitation of a solid starts.

A total of 80 ml of hexane is added, dropping quickly in two fractions with a 30 minute interval. 22.9 g of product, as a white powder (yield 93%; m.p. 215–218°C.) are obtained by filtration.

Analogously is prepared:

2-[[4-butyl-2-methyl-6-oxo-5-[[2'-(1H-tetrazol-5-yl)-[1,1'-biphenyl]-4-yl]methyl]-1(6H)-pyrimidinyl]methyl]-3-furancarbonitrile sodium salt (m.p. 110–113° C.).

EXAMPLE 4

2-[[4-butyl-2-methyl-6-oxo-5-[[2'-[[(trifluoromethyl)-sulfonyl]amino]-[1,1'-biphenyl]-4-yl]methyl]-1(6H)-pyrimidinyl]methyl]-3-furancarbonitrile Part A A solution of 0.43 g of 2-[[4-butyl-2-methyl-6-oxo-5-[[2'-nitro-[1,1'-biphenyl]-4-yl]methyl]-1(6H)-pyrimidinyl] methyl]-3-furancarbonitrile in 10 ml of 95% ethanol is hydrogenated in the presence of 40 mg of 10% palladium-on-charcoal, under atmospheric pressure and at room temperature. After the calculated hydrogen absorption, the catalyst is filtered through celite$^R$ and the solvent is evaporated off under reduced pressure, to obtain 0.36 g of a pale yellow spongy solid which is reacted directly (90% yield).

$^1$H-NMR δ: 089 (t,3H), 1.21–1.75 (m,4H), 2.58 (t,2H), 2.59 (s,3H), 3.96 (s,2H), 5.39 (s,2H), 6.58 (d,1H), 6.67–6.84 (m,2H), 6.99–7.48 (m,6H), 7.42 (d,1H).

Part B

A solution of 0.33 g of 2-[[4-butyl-2-methyl-6-oxo-5-[[2'-amino[1,1'-biphenyl]-4-yl]methyl-1(6H)-pyrimidinyl]- methyl-3-furancarbonitrile in 3 ml of anhydrous $CH_2Cl_2$, cooled at −78° C., is added, drop by drop with 74 mg of triethylamine and 0.14 ml of trifluoromethanesulfonic anhydride with stirring and under inert atmosphere. After 1 h the reaction is quenched by addition of some drops of water and is left to warm to room temperature. The organic phase is separated from the aqueous one, washed with a slightly alkaline solution to adjust pH at 7 and with a NaCl saturated solution, then dried over $Na_2SO_4$. The solvent is evaporated off under reduced pressure, to obtain 0.42 g of a spongy solid residue which, after flash chromatography (hexane-AcOEt 50:50), yields 0.21 g of a whitish solid (49% yield, m.p. 65–75° C. dec).

EXAMPLE 5

2-[[4-butyl-2-methyl-6-oxo-5-[[2'-[1-(triphenylmethyl)-1H-tetrazol-5-yl]-[1,1'-biphenyl]-4-yl]methyl]-1(6H)-pyrimidinyl]methyl]-N-methyl-3-pyridinecarboxamide A suspension of 0.35 g of 2-[[4-butyl-2-methyl-6-oxo-5-[[2'[1(triphenylmethyl)-1H-tetrazol-5-yl][1,1'-biphenyl]-4-yl]methyl]-1(6H)-pyrimidinyl]methyl]-3-pyridinecarboxylic acid in 4 ml of anhydrous THF is added with 0.22 g of carbonyldiimidazole. After 30 minutes under magnetic stirring, the resulting solution is added with 2.25 ml of a 2M methylamine solution in THF. When the reaction is complete (≅7 h), the solvent is evaporated off under reduced pressure, the residue is taken up with $H_2O$, to obtain a solid which is filtered and purified by flash chromatography ($CH_2Cl_2$—$CH_3OH$: 97-3), to obtain 0.3 g of a spongy solid (85% yield, m.p. 195–197° C. dec. ($CH_3OH$). $^1$H-NMR ($CDCl_3$) δ0.87 (t,3H), 1.18–1.70 (m,4H), 2.43 (t,2H), 2.78 (s,3H), 2.98 (d,3H), 3.76 (s,2H), 5.30 (s,2H), 6.75–6.98 (m,9H), 7.10–7.48 (m,14H), 7.80–7.91 (m,2H), 8.48 (dd,1H), 8.57–8.72 (m,1H).

Analogously are prepared:

2-[[4-butyl-2-methyl-6-oxo-5-[[2'-[1-(triphenylmethyl)-1H-tetrazol-5-yl][1,1'-biphenyl]-4-yl]methyl]-1(6H)-pyrimidinyl]methyl]-N-methyl-3-thiophenecarboxamide (m.p. 178–180° C. dec.), 4-[[4-butyl-2-methyl-6-oxo-5-[[2'-[1-(triphenylmethyl)-1H-tetrazol-5-yl][1,1'-biphenyl]-4-yl]methyl]-1(6H)-pyrimidinyl]methyl]-N-methyl-5-thiazolecarboxamide, 2-[[4-butyl-2-methyl-6-oxo-5-[[2'-[1-(triphenylmethyl)-1H-tetrazol-5-yl][1,1'-biphenyl]-4-yl]methyl]-1(6H)-pyrimidinyl]methyl]-3-thiophenecarboxamide (m.p. 180–182° C. dec.), 2-[[4-butyl-2-methyl-6-oxo-5-[[2'-[1-(triphenylmethyl)-1H-tetrazol-5-yl[]1,1'-biphenyl]-4-yl]methyl]-1(6H)-pyrimidinyl]methyl]-3-furancarboxamide, 2-[[4-butyl-2-methyl-6-oxo-5-[[2'-[1-(triphenylmethyl)-1H-tetrazol-5-yl][1,1'-biphenyl]-4-yl]methyl]-1(6H)-pyrimidinyl]methyl]-3-pyridinecarboxamide.

EXAMPLE 6

2-[[4-butyl-2-methyl-6-oxo-5-[[2'-[1-(triphenylmethyl)-1H-tetrazol-5-yl][1,1'-biphenyl]4-yl]methyl]-1(6H)-pyrimidinyl]methyl]-3-thiophenemethanol A solution of 2 g of methyl 2-[[(4-butyl-2-methyl-6-oxo-5-[[2'[1-triphenylmethyl)-1H-tetrazol-5-yl][1,1'-biphenyl]-4-yl]methyl]-1(6H)-pyrimidinyl]methyl]-3-thiophenecarboxylate in 20 ml of anhydrous THF is added drop by drop with 1.25 ml of a 1M solution of $LiAlH_4$ in THF, under inert atmosphere and with stirring. After 30 minutes the reaction is quenched with some drops of water and the solvent is evaporated off under reduced pressure. The residue is added with 10 ml of water, 0.8 ml of 3N NaOH and 10 ml of AcOEt. After the solid at the interphase has been filtered off, the organic phase is separated and the aqueous phase is re-extracted with AcOEt. The combined organic extracts are washed with a NaCl saturated solution, dried over $Na_2SO_4$ and evaporated under reduced pressure, to give g 1.73 of a spongy white solid (89% yield). $^1$H-NMR ($CDCl_3$) δ: 0.87 (t,3H), 1.15–1.65 (m,4H), 2.46 (t,2H), 2.73 (s,3H), 3.76 (s,2H), 4.71 (s,2H), 5.40 (s,2H), 7.85–7.10 (m,10H), 7.18–7.52 (m,14H), 7.81–7.93 (m,1H).

What is claimed is:

1. Compounds of general formula I

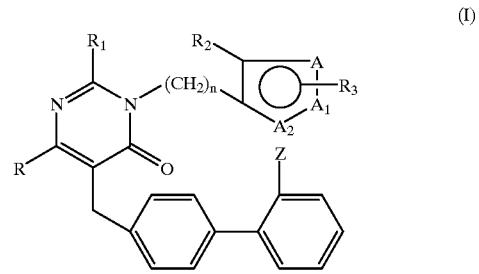

(I)

wherein:

R represents a straight, branched or cyclic lower alkyl of 1 to 5 carbon atoms, optionally substituted by a $OR_4$ group, where $R_4$ represents hydrogen or a $C_1$–$C_4$ alkyl; or a lower alkenyl group of up to 5 carbon atoms, $R_1$ and $R_3$ represent independently hydrogen or a $C_1$–$C_4$ alkyl, $R_2$ represents a CN group; a $CH_2OR_5$ group wherein $R_5$ represents hydrogen or a $C_1$–$C_4$ alkyl; a $COR_6$ group wherein $R_6$ represents a $C_1$–$C_4$ alkyl or a $NR_7R_5$ group wherein $R_7$ and $R_8$, which are the same or different, represent hydrogen, $C_1$–$C_4$ alkyl, phenyl or benzyl, n represents 1 or 2, A, $A_1$, $A_2$, represent independently N, O, S atoms, or $(CH)_m$, wherein m=1, 2, with the proviso that at least one be a heteroatom, and they form, together with two carbon atoms, a 5- or 6-membered heterocyclic ring, Z represents a $COOR_9$ group, wherein $R_9$ represents hydrogen or a $C_1$–$C_4$ alkyl; a $NHSO_2CF_3$ group; a CN group; a $NO_2$ group; a $SO_2NHR_{10}$ group, wherein $R_{10}$ represents hydrogen, $COR_{11}$, wherein $R_{11}$ represents an optionally substituted phenyl, a $C_1$–$C_4$ alkyl, a $C_1$–$C_4$ alkoxy, or $CONHR_{12}$, where $R_{12}$ is a straight or branched $C_1$–$C_4$ alkyl; a tetrazol-5-yl group;

and the pharmaceutically acceptable salts thereof.

2. Compounds according to claim 1, wherein A, $A_1$ and $A_2$ are selected so as to form, with the carbon atoms they are bound to, the following heterocyclic rings: furan, thiophene, thiazole, isothiazole, oxazole, isoxazole, pyridine, pyrimidine, pyrazine, pyridazine.

3. Compounds of formula I according to claim 1 wherein:

R is a straight, branched or cyclic lower alkyl of 1 to 5 carbon atoms, optionally substituted by a $OR_4$ group, wherein $R_4$ represents hydrogen or a $C_1$–$C_4$ alkyl, $R_2$ is a CN group, or a $COR_6$ group, wherein $R_6$ represents a $C_1$–$C_4$ alkyl or a $NR_7R_8$ group, wherein $R_7$ and $R_8$, which are the same or different, represent hydrogen, $C_1$–$C_4$ alkyl, n is 1, and Z represents a COOR$_9$ group, wherein R$_9$ represents hydrogen or a C$_1$–C$_4$ alkyl; a NHSO$_2$CF$_3$ group; a tetrazol-5-yl group, optionally protected by a group selected from the following: triphenylmethyl, tert-butyl, C$_1$–C$_4$ alkoxymethyl, 4-methoxybenzyl, 2,4,6-trimethylbenzyl, tetrahydropyranyl or 2-trimethylsilylethyl;

and the pharmaceutically acceptable salts thereof.

4. Compounds of formula I according to claim 3 wherein:

R is a lower alkyl of 1 to 5 carbon atoms,

R$_2$ represents a CN group or a CONR$_7$R$_8$ group, wherein R$_7$ and R$_8$, which are the same or different, represent can be hydrogen or C$_1$–C$_4$ alkyl, n is 1;

Z is a tetrazol-5-yl group.

5. Compounds according to claim 3 which are:

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-furancarbonitrile;

2-[[4-butyl-2-methyl-6-oxo-5-[[2'-(1H-tetrazol-5-yl)[1,1'-biphenyl]-4-yl]methyl]-1(6H)-pyrimidinyl]-methyl] 3-thiophenecarbonitrile;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-3-pyridinecarbonitrile;

4-[[4-butyl-2-methyl-6-oxo-5-[[2'-(1H-tetrazol-5-yl)[1,1'-biphenyl]-4-yl]methyl]-1(6H)-pyrimidinyl]-methyl]-5-thiazolecarbonitrile;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-pirazincarbonitrile;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-pyridinecarboxamide;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-furancarboxamide;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-3-thiophenecarboxamide;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-N-methyl-3-thiophenecarboxamide;

2-[[4-butyl-2-methyl-6-oxo-5-[[2'-(1H-tetrazol-5-yl)[1,1'-biphenyl]-4-yl]methyl]-1(6H)-pyrimidinyl]-methyl]-N-methyl-3-pyridinecarboxamide;

4-[[4-butyl-2-methyl-6-oxo-5-[[2'-(1H-tetrazol-5-yl)[1,1'-biphenyl]-4-yl]methyl]-1(6H)-pyrimidinyl]-methyl]-N-methyl-5-thiazolecarboxamide and the pharmaceutically acceptable salts thereof.

6. Pharmaceutical compositions which comprise as the active ingredient an effective amount of a compound according to claims 1 together with a suitable pharmaceutical excipient.

7. The use of a compound according to claim 1 for the preparation of a medicament for use in the treatment of angiotensin II (AII)—mediated diseases.

* * * * *